United States Patent [19]

Lutz

[11] 4,341,223
[45] Jul. 27, 1982

[54] FLUORESCEABLE COMPOSITION AND METHOD OF DETERMINING FLUID FLOW

[76] Inventor: Lauralee A. Lutz, 2925 Hilltop, Ann Arbor, Mich. 48104

[21] Appl. No.: 231,039

[22] Filed: Feb. 4, 1981

[51] Int. Cl.³ .......................... A61B 5/00; C09K 11/06
[52] U.S. Cl. .............................. 128/666; 252/301.19; 252/301.32; 424/7; 424/9
[58] Field of Search .............................. 128/633, 666; 252/301.19, 301.32; 424/7, 9

[56] References Cited

U.S. PATENT DOCUMENTS 3,541,201  11/1970  Brown ........................................ 424/7
4,115,536   9/1978  Rothman et al. ........................ 424/9

OTHER PUBLICATIONS

Merck Index, 9th Edition, No. 3621, p. 485, 1976.

Primary Examiner—Allan Lieberman
Attorney, Agent, or Firm—Olsen and Stephenson

[57] ABSTRACT

A fluoresceable composition in dosage unit form and method for determining fluid or blood flow are provided for medical, surgical or diagnostic purposes, using 6, 7-dihydroxycoumarin 6-glucoside which in vivo is invisible in natural light and is highly visible as a blue-white color in ultraviolet light. The composition and method enable "reading", visualization, diagnosis, demarcation, assessment, etc., of adequacy of blood supply, vasculature and fluid flow; loss of fluid; viability of tissue, skin and organs or aspects thereof; and the like.

13 Claims, No Drawings

FLUORESCEABLE COMPOSITION AND METHOD OF DETERMINING FLUID FLOW

BACKGROUND OF THE INVENTION

1. Field of the Invention

This invention relates to a fluoresceable composition in dosage unit form and to a method, for medical surgical or diagnostic purposes, particularly for determining fluid or blood flow of a subject as visualized by fluorescence in ultraviolet light.

2. Prior Art

The clinical use of fluorescein sodium under ultraviolet light as a fluorescent indicator of blood supply, vasculature and tissue viability is conventional in the field of plastic and reconstructive surgery, and opthalmology. However, fluorescein sodium is not useful in heavily pigmented, non-Caucasion tissue, due to its limited fluorescence. Furthermore, fluorescein sodium may persist in tissue for days, thus limiting its usefulness as a fluorescing substance to a single intra-operative injection. Also, fluorescein sodium is a dye which temporarily can give the skin an unnatural color under normal light.

It is therefore an object of the present invention to provide improved means for determining fluid or blood flow in vivo, as visualized by fluorescence in ultraviolet light, particularly for medical, surgical or diagnostic operations or procedures.

It is also an object of the invention to provide such means which enables brighter fluorescence and better visualization.

It is a further object of the invention to provide such means which enables short term fluorescent visualization.

It is a still further object to provide means of visualization which is color-free for skin, clothing, etc., under natural light.

These and other objects, features and advantages will be seen from the following detailed description of the invention.

SUMMARY AND DETAILED DESCRIPTION

One aspect of the present invention concerns an aqueous fluoresceable composition comprising 6, 7-dihydroxycoumarin 6-glucoside in parenteral dosage unit form at a concentration sufficient, when administered to a subject and exposed to ultraviolet light, for visualizing fluorescence of flowing tissue fluid, particularly fluid flow at superficial skin and tissue sites. As used herein, the term "tissue fluid" is meant to include blood, spinal fluid, and the like. The composition of the invention is particularly useful in plastic and reconstructive surgery, and opthalmalogy. It can be used in substantially the same way as conventional fluorescein sodium compositions now available and is at least equally reliable. The present composition, unlike fluorescein sodium compositions, is colorless in natural light, both in vitro and in vivo. It is constituted in parenteral dosage form and is preferably administered by the intravenuous route for prompt distribution in vivo to the site requiring visualization.

A suitable composition, for example, is a sterile aqueous 2% solution of 6, 7-dihydroxycoumarin 6-glucoside (The Merck Index, Mon. No. 3621, 9th Ed.) made by dissolving 2.0 g. of the latter with thorough mixing in 100 ml. of normal sodium hydroxide, then adjusting to pH 7 by neutralizing with normal hydrochloric acid. The composition may also include a neutral buffer.

As indicated, another aspect of the invention concerns a method for determining fluid flow in a subject, comprising administering to the subject a fluoresceable composition in parenteral dosage unit form comprising 6, 7-dihydroxycoumarin 6-glucoside, exposing the treated subjected to ultraviolet light, and viewing the subject while exposed to determine the presence and distribution of fluorescence. Following administration, the fluorescence characteristically persists for a period which is sufficiently long for diagnostic and surgical purposes. By comparison with fluorescein sodium compositions, one can use approximately half the usual dose of fluorescein sodium, yet the present composition acts roughly twice as quickly in establishing adequately fluorescent blood levels and with a peak fluorescence that is at least twice as bright, being easily read even in a room with overhead visible spectrum lights. By further comparison, fluorescence in the black skinned subject is significantly easier to interpret than that of fluorescein sodium under the same conditions. Further, the present composition is absolutely colorless in the skin when viewed in natural light. Advantageously, 6,7-dihydroxycoumarin 6-glucoside clears the body in about half the time that it takes fluorescein sodium to disappear. This means that in accordance with the present invention, one can reinject the same subject in the early postoperative period to monitor the surgical results, which is impossible to do with fluorescein sodium due to the residual fluorescent color. However, the present composition advantageously is mutually compatible with fluorescein sodium compositions. Both can be used in the same operation and do not scavenge each other. In a plastic surgergy operation, for example, where both agents are used, each according to the present invention can accurately assess the blood flow, and each can thereby predict the viability of a given skin flap or a redesigned version thereof, yet retain its separate color under ultraviolet light. In fact, the invention contemplates the procedure of using both the present composition and one such as a fluorescein sodium composition during a single operation wherein one composition is injected first when the skin flap is elevated to assess viability, then the flap is redesigned if the blood supply seems from the first assessment to be compromised, and finally the other composition is injected to see in a second reading if the redesigned flap is more likely to survive. In this regard, the invention is particularly applicable to reconstructed tissue, transplanted tissue, traumatized tissue, and the like.

The composition and method of the invention are applicable to mammalian species, being well tolerated, for example, in the rat, dog and pig. In general, one uses the composition in a dose or amount of 6, 7-dihydroxycoumarin 6-glucoside sufficient to establish a fluid level or blood level that will enable superficial fluorescent visualization. From general considerations which will be well understood in the art, this amount in a given case will vary depending on several factors such as route of administration, subject species, subject body weight, skin color and maturity (whether adult or non-adult). An indicated minimum intravenous dosage for humans is about 6 to 10 mg./kg. of body weight for adults and about 3 to 5 mg./kg. of body weight for children.

An exemplary procedure for assessment of skin flap blood supply in an 70 kg. adult white subject is as follows: A 2% aqueous solution of 6, 7-dihydroxycoumarin 6-glucoside, prepared as described above, in the amount of 30 cc. is administered intravenously (antecubital vein) over a five minute period after the skin flap is elevated and secured to its bed. The flap is viewed under ultraviolet light (such as that afforded by a mercury vapor lamp, e.g., Model B 100A, Ultra-Violet Products, Inc.) preferably with reduced visual light. This is done periodically, before injection, immediately after, and until the entire vascular area of the flap fluoresces, after 10-, 20- and 30-minute intervals after injection. The steady state distribution of fluorescence is observed and measured if necessary for redesign based on an assessment of viability. The procedure is repeated postoperatively, if desired, to monitor the surgical results.

For purposes of retinal angiography, whereby the status of the internal vasculature of the eye is evaluated, a similar technique is used. For example, a 70 kg. adult white diabetic patient may undergo intravenous injection of 30 cc. of the previously described solution. A photographic assessment of the integrity of the retinal vasculature is then made, utilizing standard ultraviolet intraocular photo technique.

Other ophthalmologic applications include uses in applanation tonometry and the diagnosis of corneal disorders. For example, an appropriate concentration of the composition of the invention may be applied in solution directly to the cornea of the eye. Alternatively, a paper strip impregnated with the composition of the invention may be placed in contact with the cornea. Normal cornea will not stain, while ulcers or parts deprived of epithelium with fluoresce when viewed with ultraviolet light. Defects or disease of the corneal epithelium stain brightly. The dye is also useful in testing lacrimal system patency, the stain appearing nasally if the drainage system is intact.

It is understood that, while the invention has been described in detail with reference to specific embodiments, various changes and modifications thereof within the skill of the art may be made and that all such changes and modifications are intended to be within the scope of the following claims.

What is claimed is:

1. An aqueous fluoresceable composition comprising 6, 7-dihydroxycoumarin 6-glucoside in parenteral dosage unit form at a concentration sufficient, when administered to a subject and exposed to ultraviolet light, for visualizing fluorescence in tissue fluid, the composition being adapted for co-administration with fluoresceable parenteral fluorescein and being compatible and non-scavenging with said fluorescein in vivo.

2. An aqueous fluoresceable diagnostic composition comprising 6, 7-dihydroxycoumarin 6-glucoside in intravenous dosage unit form at a concentration sufficient, when administered to a subject and exposed to ultraviolet light, for visualizing fluorescence of blood flow, the composition being adapted for coadministration with fluoresceable parenteral fluorescein and being compatible and non-scavenging with said fluorescein in vivo.

3. An aqueous fluoresceable diagnostic composition comprising 6, 7-dihydroxycoumarin 6-glucoside in intravenous dosage unit form at a concentration sufficient, when administered to a subject and exposed to ultraviolet light, for photographing fluorescence of blood flow, as in retinal angiography, the composition being adapted for co-administration with fluoresceable parenteral fluorescein and being compatible and non-scavenging with said fluorescein in vivo.

4. An aqueous fluoresceable pharmaceutical composition comprising 6, 7-dihydroxycoumarin 6-glucoside in parenteral dosage unit form at a concentration sufficient, when administered to a subject and exposed to ultraviolet light, for visualizing blood flow and tissue viability at a surgical site, the composition being adapted for co-administration with fluoresecable parenteral fluorescein and being compatible and non-scavenging with said fluorescein in vivo.

5. A method for determining fluid flow in a subject comprising administering to the subject a fluoresceable composition in parenteral dosage unit form comprising 6, 7-dihydroxycoumarin 6-glucoside, exposing the treated subject to ultraviolet light, and viewing the subject while exposed to determine the presence and distribution of fluorescence.

6. A method for determining blood flow in a subject's tissue comprising administering to the subject a fluoresceable composition in parenteral dosage unit form comprising 6, 7-dihydroxycoumarin 6-glucoside, exposing the treated tissue to ultraviolet light, and viewing the tissue while exposed to determine the presence and distribution of fluorescence.

7. A method according to claim 6 where the tissue is reconstructed tissue.

8. A method according to claim 6 where the tissue is transplanted tissue.

9. A method according to claim 6 where the tissue is traumatized tissue.

10. A method for determining fluid flow in a subject's tissue comprising administering to the subject a fluoresceable composition in parenteral dosage unit form comprising 6, 7-dihydroxycoumarin 6-glucoside, exposing the treated tissue to ultraviolet light, and viewing the tissue while exposed to determine the presence and distribution of fluorescence.

11. A method according to claim 10 where the tissue is skin tissue.

12. A method according to claim 10 when the tissue is the retina or cornea of the eye.

13. A method according to claim 10 where the integrity or adequacy of vascularity is assessed.

* * * * *